United States Patent
Talutis

(10) Patent No.: US 8,568,575 B2
(45) Date of Patent: Oct. 29, 2013

(54) ADJUSTABLE, RETRACTABLE PROBE INSERTION ASSEMBLY

(75) Inventor: Stephen B. Talutis, Milton, MA (US)

(73) Assignee: Invensys Systems, Inc., Foxboro, MA (US)

( * ) Notice: Subject to any disclaimer, the term of this patent is extended or adjusted under 35 U.S.C. 154(b) by 431 days.

(21) Appl. No.: 12/842,729

(22) Filed: Jul. 23, 2010

(65) Prior Publication Data

US 2011/0048942 A1    Mar. 3, 2011

Related U.S. Application Data

(60) Provisional application No. 61/239,274, filed on Sep. 2, 2009.

(51) Int. Cl.
| | | |
|---|---|---|
| B23H 7/26 | (2006.01) | |
| B23H 11/00 | (2006.01) | |
| C25B 9/00 | (2006.01) | |
| C25C 7/00 | (2006.01) | |
| C25D 17/00 | (2006.01) | |
| C25F 7/00 | (2006.01) | |

(52) U.S. Cl.
USPC ............. 204/297.01; 204/286.1; 204/297.15; 204/400; 204/409; 73/866.5

(58) Field of Classification Search
USPC ........... 204/286.1, 409, 297.15, 400, 297.01; 73/866.5
See application file for complete search history.

(56) References Cited

U.S. PATENT DOCUMENTS

| | | | |
|---|---|---|---|
| 3,463,012 A | 8/1969 | McKinney et al. | |
| 4,012,308 A | 3/1977 | Jerrold-Jones et al. | |
| 4,273,637 A | 6/1981 | MacDonald et al. | |
| 4,657,657 A | 4/1987 | Stellmacher | |
| 4,978,921 A | 12/1990 | Indig et al. | |
| 5,565,076 A * | 10/1996 | Topping et al. | 204/419 |
| 5,830,338 A | 11/1998 | Seto et al. | |
| 6,236,880 B1 | 5/2001 | Raylman et al. | |
| 6,398,931 B1 | 6/2002 | Burchette et al. | |
| 6,423,197 B1 | 7/2002 | Lenferink et al. | |
| 6,579,440 B2 | 6/2003 | Connelly et al. | |
| 6,616,821 B2 | 9/2003 | Broadley et al. | |

(Continued)

OTHER PUBLICATIONS

Product Website for Yokogawa PH87. available: http://web.archive.org/web/20051020235354/http://www.yokogawa.com/us/ia/analytical/us-ykgw-anal-ph87-pdetail.htm.*

(Continued)

Primary Examiner — Luan Van
Assistant Examiner — Louis Rufo
(74) Attorney, Agent, or Firm — Edward S. Jarmolowicz, Esq.

(57) ABSTRACT

An adjustable insertion assembly for an electrochemical sensor includes an electrode holder to receive the sensor, having a distal aperture to permit process fluid to contact the sensor. A receptacle slidably receives the holder, for a sliding range of motion extending from fully inserted to fully retracted positions. An open distal end portion of the receptacle extends through a wall of a process fluid vessel, so that the aperture is open to the process fluid when fully inserted, and closed when fully retracted. A leverage member is releasably movable relative to the receptacle, and moves with a captured extension. An abutment of the receptacle engages the extension so that movement of the leverage member in opposite directions alternately clamps and releases the electrode holder relative to the receptacle to substantially prevent and permit movement at substantially any point within the range of movement.

21 Claims, 4 Drawing Sheets

(56) References Cited

U.S. PATENT DOCUMENTS

| | | |
|---|---|---|
| 6,634,494 B1 | 10/2003 | Derr et al. |
| 6,653,926 B1 | 11/2003 | Zitzmann |
| 7,135,870 B2 | 11/2006 | Mohajer et al. |
| 7,182,847 B1 | 2/2007 | Millar et al. |
| 2002/0011422 A1 | 1/2002 | Meier |
| 2002/0083977 A1 | 7/2002 | Beck et al. |
| 2005/0011771 A1 | 1/2005 | Wittkampf et al. |
| 2005/0019219 A1 | 1/2005 | Oshiman et al. |
| 2005/0223829 A1 | 10/2005 | Mayeaux |
| 2005/0229727 A1 | 10/2005 | Caderas |
| 2006/0027453 A1 | 2/2006 | Catalano et al. |
| 2006/0096862 A1 | 5/2006 | Benton |
| 2006/0249386 A1 | 11/2006 | Bower et al. |
| 2007/0034028 A1* | 2/2007 | Tottewitz et al. ............ 73/866.5 |
| 2007/0221498 A1 | 9/2007 | Woodward et al. |

OTHER PUBLICATIONS

Product Documentation for PH87 Genreal Specifications.*
Product Documentation for PH87 Inctruction Manual.*
PCT International Search Report regarding PCT/US2011/044987 dated Jan. 30, 2012, 2 pages.
Written Opinion regarding International Application No. PCT/US2011/044987 dated Jan. 30, 2012, 6 pages.
Office action issued Oct. 16, 2012 in related U.S. Appl. No. 12/869,252, 26 pgs.

* cited by examiner

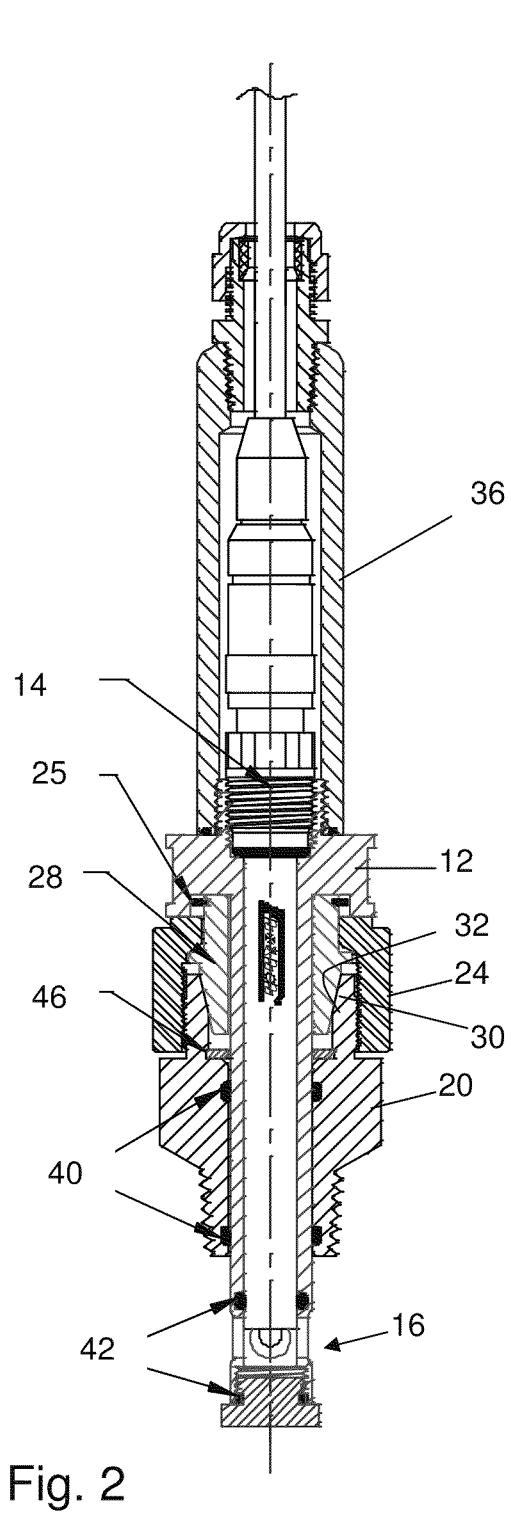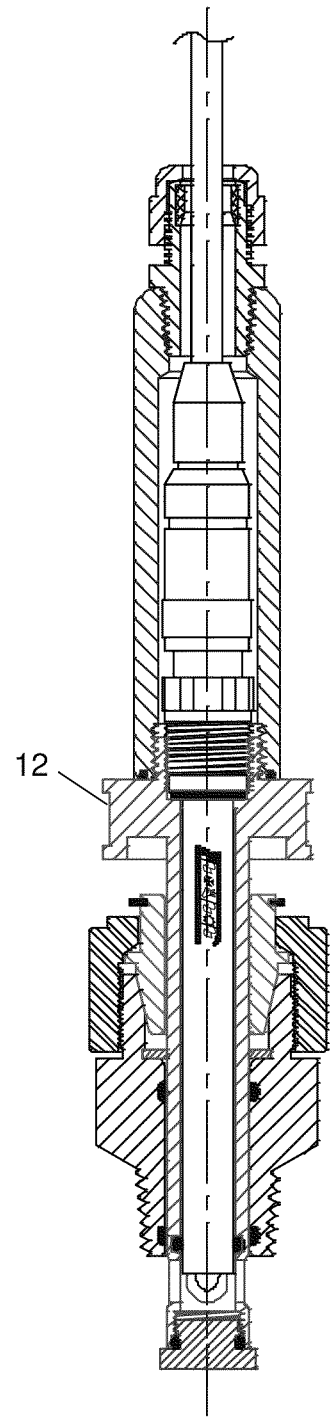
Fig. 2
Fig. 3

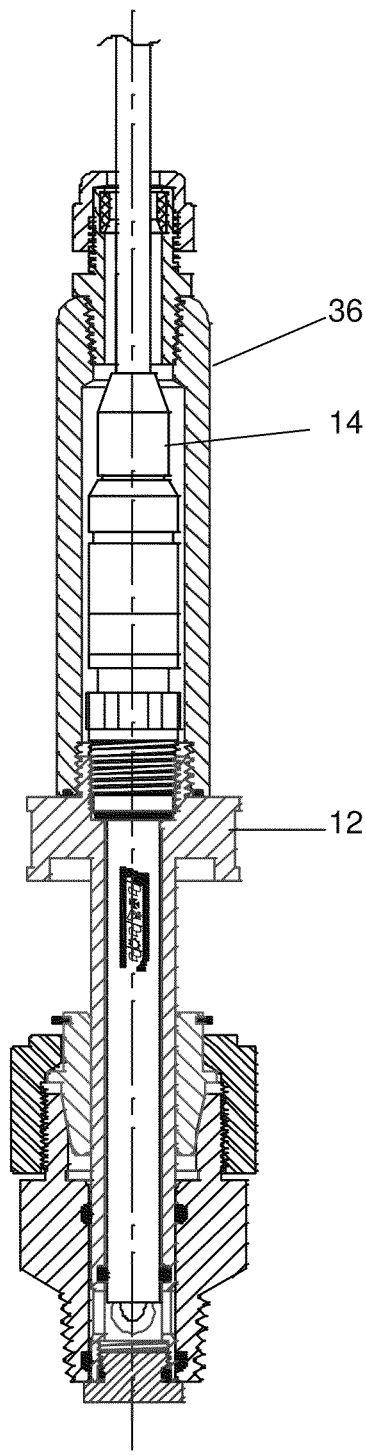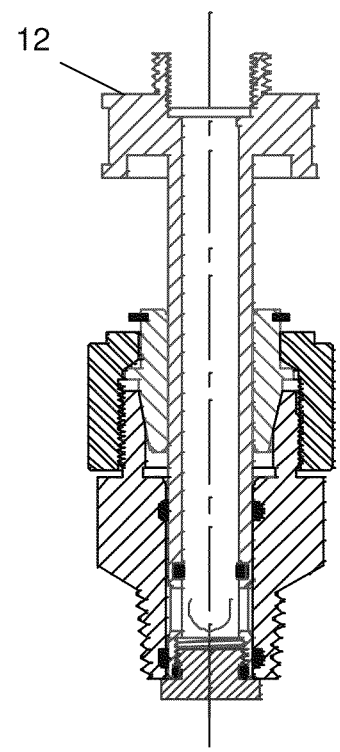
Fig. 4
Fig. 5

ADJUSTABLE, RETRACTABLE PROBE INSERTION ASSEMBLY

RELATED APPLICATION

This application claims the benefit of U.S. Provisional Application Ser. No. 61/239,274, entitled Robust pH Sensor, filed on Sep. 2, 2009, the contents of which are incorporated herein by reference in their entirety for all purposes.

BACKGROUND

1. Technical Field

This invention relates to sensor probes used in the process analytical industry, and more particularly to a retractable assembly for enabling adjustable insertion and retraction of electrochemical sensors to and from a fluid process without requiring shut-down of the process.

2. Background Information

Retractable insertion assemblies are used in the process analytical industry to enable insertion and retraction of sensor probes under process pressure and temperature conditions without leakage of process fluid. Retraction may be carried out in order to replace or perform maintenance or calibration of probes.

Insertion assemblies for conventional 12 mm diameter pH sensors typically have two positions—inserted and retracted. During insertion/retraction, the sensor probe is placed within a central shaft of the insertion assembly. This central shaft is axially slidable between the two positions. A pair of o-rings may be placed around the central shaft to provide a fluid-tight seal that helps prevent leakage of the process fluid in both positions and as the shaft moves between the inserted and retracted positions. The inserted and retracted positions are secured by conventional quarter-turn fasteners, e.g., by pins that are engaged upon a quarter turn of the shaft.

This approach may perform satisfactorily when used with probes having a specific fixed length and fixed insertion depth in the process fluid. However, this approach is not intended to accommodate probes of varying length and/or applications involving variable depths of insertion into the process.

A need therefore exists for an improved insertion assembly that addresses one of more of the foregoing issues associated with conventional approaches.

SUMMARY

One aspect of the present invention includes an adjustable insertion assembly for modular electrochemical potential measurement sensors. The assembly includes an elongated electrode holder, configured to receive therein an electrochemical sensor having measurement and reference half cells, the electrochemical sensor configured for electrochemically responding to a process analyte upon contact with a process fluid. A receptacle is configured to slidably receive the electrode holder therein, so that the holder is slidable within a range of motion extending from inserted to retracted positions. The receptacle has an open distal end portion configured for extension through a wall of a process fluid vessel, so that the electrode holder is open to the process fluid when the electrode holder is in inserted positions, and closed to the process fluid when in the retracted position. A leverage member is coupled to the receptacle and configured for releasable movement relative to the receptacle. An extension captured by the leverage member is movable by the leverage member. The receptacle has an abutment configured to engage the extension in a sliding, interference fit, so that movement of the leverage member in opposite directions alternately clamps and releases the electrode holder relative to the receptacle to substantially prevent and permit movement at substantially any point within the range of movement.

Another aspect of the invention employs the foregoing embodiment in a method of adjustably inserting an electrochemical potential measurement sensor into a process fluid. This method includes extending the open distal end portion of the receptacle through a wall of a process fluid flow conduit, placing the electrochemical sensor into the elongated electrode holder, and slidably placing the electrode holder into the receptacle, so that the electrode holder is slidable within a range of motion extending from an inserted position in which the aperture of the electrode holder is open to process fluid within the conduit, to a retracted position in which the aperture of the electrode holder is closed to the process fluid. The method further includes sliding the electrode holder into a fluid insertion position at any of a plurality of locations within its range of motion, and clamping, with the leverage member, the electrode holder in the fluid insertion position. The electrochemical sensor is operated to detect an analyte associated with the process fluid. The leverage member is then used to release the electrode holder, which is then moved into the retracted position to close the aperture to the process fluid. The holder may then be clamped, with the leverage member, in the retracted position, for removal and replacement of the sensor. The placed sensor may then be moved into an insertion position for analyte measurement as described above.

The features and advantages described herein are not all-inclusive and, in particular, many additional features and advantages will be apparent to one of ordinary skill in the art in view of the drawings, specification, and claims. Moreover, it should be noted that the language used in the specification has been principally selected for readability and instructional purposes, and not to limit the scope of the inventive subject matter.

BRIEF DESCRIPTION OF THE DRAWINGS

The present invention is illustrated by way of example and not limitation in the figures of the accompanying drawings, in which like references indicate similar elements and in which:

FIG. 2 is an axial cross-sectional view taken along 2-2 of FIG. 1;

FIG. 3 is a view similar to that of FIG. 2, in a partially inserted position;

FIG. 4 is a view similar to those of FIGS. 2 and 3, in a fully retracted position;

FIG. 5 is a view similar to that of FIG. 4, with the electrochemical sensor removed therefrom.

DETAILED DESCRIPTION

In the following detailed description, reference is made to the accompanying drawings that form a part hereof, and in which is shown by way of illustration, specific embodiments in which the invention may be practiced. These embodiments are described in sufficient detail to enable those skilled in the art to practice the invention, and it is to be understood that other embodiments may be utilized. It is also to be understood that structural, procedural and system changes may be made without departing from the spirit and scope of the present invention. In addition, well-known structures, circuits and techniques have not been shown in detail in order not to obscure the understanding of this description. The following detailed description is, therefore, not to be taken in a limiting sense, and the scope of the present invention is defined by the appended claims and their equivalents.

General Overview

An adjustable, retractable sensor insertion assembly and method are described. In the following description, for purposes of explanation, numerous specific details are set forth in order to provide a thorough understanding of the present invention. It will be evident, however, to one skilled in the art that the present invention may be practiced without these specific details.

The present invention relates to electrochemical probes such as those commonly used for measurement of pH, ORP, conductivity, dissolved oxygen, ions, or other chemical species and/or analytes. Embodiments of this invention improve upon prior art by accommodating different length probes and/or allowing users to adjust the depth of insertion to any of various positions between a maximum and minimum insertion depth. Indeed, particular embodiments provide a substantially "infinite" adjustability, in which the user is not limited to specific, predefined positions, but rather, may select substantially any location between the maximum and minimum positions.

In particular exemplary approaches, this adjustability may be accomplished by the use of a wedge/cam system, such as in the form of a split ferrule which is compressible into an interference fit, to secure the shaft at nominally any point within a range of motion extending from (e.g., fully) retracted to (e.g., fully) inserted positions. These embodiments enable a user to change the insertion depth of a given probe/insertion assembly combination as desired, such as to accommodate varying levels of process fluid within a conduit, pressure vessel, or other fluid container, and/or to permit measurement at different levels within the fluid where conditions may vary. These embodiments may also enable a single insertion assembly to accommodate probes of different lengths, to provide further versatility.

TERMINOLOGY

Figure 1:
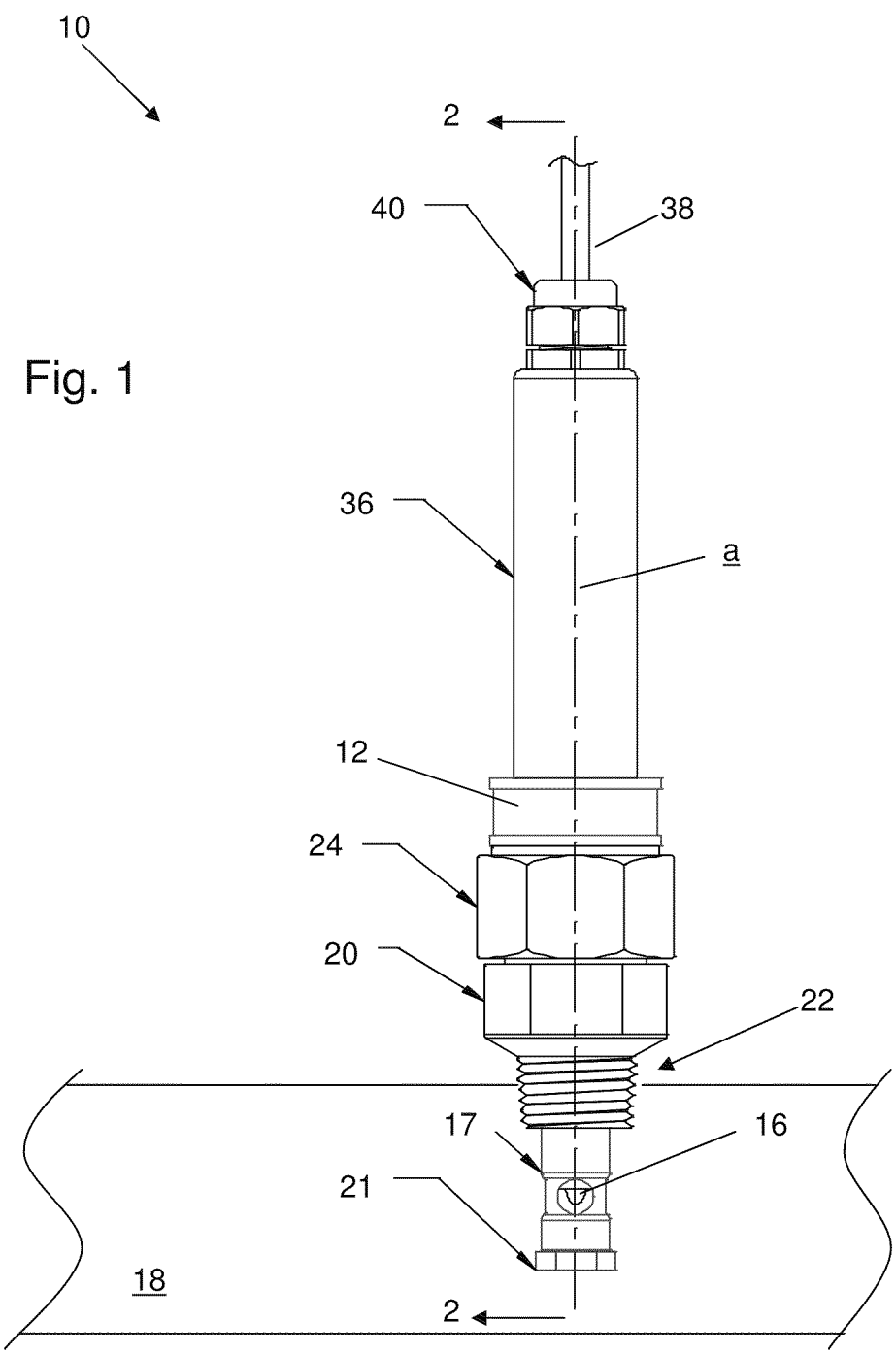
FIG. 1 is an elevational view of an embodiment of the insertion assembly of the present invention, in a fully inserted position, and including an electrochemical sensor disposed therein.

For the purposes of the present specification, the term "axial" when used in connection with an element described herein, refers to a direction relative to the element, which is substantially parallel to axis a when the element is installed on the assembly as shown in FIG. 1. Similarly, the term "transverse" refers to a direction other than substantially parallel to the axial direction. The term "transverse circumference" refers to a circumference taken along a transverse plane. The term "fluid flow conduit" and/or "conduit" refers to substantially any structure within which a process fluid is contained, including, but not limited to, a pipe, channel, pressure vessel, or substantially any other fluid container, such as may be used for continuous and/or batch fluid processing.

Referring now to the Figures, embodiments of the present invention will be more thoroughly described. Turning in particular to FIGS. 1 and 2, a particular example of an adjustable insertion assembly for modular electrochemical potential measurement sensors is shown at 10. This assembly 10 includes an elongated electrode holder 12, configured to receive therein an electrochemical sensor 14 (FIG. 2), e.g., of the type having measurement and reference half cells, and which is configured for electrochemically responding to a process analyte upon contact with a process fluid. Examples of electrochemical sensors 14 include those disclosed in the above-referenced U.S. Provisional Patent Application Ser. No. 61/239,274, entitled Robust pH Sensor, filed on Sep. 2, 2009. These embodiments may be particularly advantageous when used with the modular sensors disclosed therein, which may be configured by the user to various lengths. Moreover, in addition to pH sensors, electrochemical sensors configured to detect substantially any analyte, including ORP (Oxidation/Reduction), conductivity, dissolved oxygen, ions (e.g., fluoride ions), or other chemical species, etc., may be used with these embodiments. Particularly useful sensors 14 may include those commercially available from Invensys Systems, Inc. (Foxboro, Mass.) which are configured for being coupled to a process variable transmitter within an automated process control system.

As shown, electrode holder 12 has one or more apertures 16 disposed in a distal end 17 thereof, to permit process fluid within a fluid flow conduit or vessel 18 to flow therethrough into contact with the sensor 14. A receptacle (ferrule seat) 20 is sized and shaped to receive the electrode holder 12 with a sliding fit, so that the electrode holder 12 is slidable within a range of motion extending from fully inserted to fully retracted positions (as shown in FIGS. 2 and 4, respectively).

As also shown, receptacle 20 has a distal end portion 22 configured for extension through a wall of a process fluid flow conduit 18. In the particular embodiment shown, distal end portion 22 is provided with a conventional pipe thread, for convenient, fluid-tight engagement with the conduit 18. It should be recognized, however, that substantially any suitable engagement may be provided without departing from the scope of the present invention.

The distal portion 22 is open to the process fluid, so that the aperture 16 of the electrode holder 12 is open to the process fluid when the electrode holder 12 is disposed in the inserted positions as shown (FIGS. 1, 2, 3). Aperture 16 is closed to the process fluid when in its fully retracted position, e.g., when the aperture 16 is moved into superposed position with the wall of the distal portion 22 as shown in FIG. 4. Optionally, a flange (e.g., shaft nut) 21 may be used to enhance closure of aperture 16 and to provide a mechanical stop when in the fully retracted position, as will be discussed in greater detail hereinbelow.

A leverage member, e.g., in the form of a tube nut 24, is coupled to the receptacle, and configured for releasable movement relative to the receptacle, such as by being threadably engaged with a proximal end of the receptacle 20, as best shown in FIG. 2. When rotated about its axis (a), nut 24 moves axially relative to the receptacle 20. An (e.g., axial) extension 28 is captured by the tube nut 24, e.g., by a retaining ring 25, and configured for (e.g., axial) movement with the tube nut 24 as a single unit relative to the receptacle 20. In a particular example, extension 28 may take the form of a wedge/cam surface 30 extending obliquely to the axial direction. A plurality of extensions/surfaces 28, 30 may be spaced circumferentially about the holder 12, e.g., on opposite sides of the holder as shown. Alternatively, extension 28 and surface 30 may take the form of a single circular (e.g., split) ferrule disposed about the electrode holder 12 as discussed in greater detail below.

As also shown, receptacle 20 includes an abutment 32 configured to engage the axial extension 28 in a sliding, interference fit, in which mutual engagement moves at least one of the extension 28 and abutment 32 in the transverse direction. In particular embodiments, the abutment 32 may take the form of a cam surface extending obliquely to the axial direction, and configured for surface to surface engagement with the cam surface 30 as shown. Movement of the tube nut 24 in opposite axial directions, i.e., by rotating about its axis, alternately moves the extension 28 and abutment 32 into and out of engagement with one another, to respectively clamp and release the electrode holder 12 relative to the receptacle 20. In other words, when the Electrode/Holder needs to be adjusted, the nut 24 may simply be loosened to remove the clamping force on the holder 12, to allow axial movement/ placement of the sensor 14, and vice versa. This configuration thus enables the holder 12 to be clamped at substantially any point within its range of movement. Such clamping may be used to substantially prevent movement of the holder 12 after insertion into the process fluid. This clamping may also be used to facilitate removal of the sensor 14, e.g., upon retraction of the holder 12, by securing the holder 12 while the handle 36 is unthreaded therefrom.

As mentioned above, it is noted that the extension 28 and surface 30 may be configured as a single device (ferrule) extending circumferentially about the holder 12. In particular embodiments, however, the ferrule may be split, and/or a plurality of extensions/surfaces may be spaced circumferentially about the holder, to provide a discontinuous transverse circumference. This provision of a discontinuous circumference, i.e., one that does not extend a full 360 degrees around the holder, tends to help prevent the extension(s) from becoming permanently bonded to the holder during use, to extend the useful life facilitate re-use of the extension 28 and holder 12.

It should be recognized that although leverage member is shown and described as a nut 24, and that the extension is shown as an axial extension 28, any number of alternate approaches may be used to provide the leverage and camming action to facilitate the adjustable clamping and unclamping described herein. For example, the leverage member and extension/cam surface may include any number of conventional quick-release mechanisms of the type commonly used to clamp and unclamp mechanical components to one another.

An electrode housing (handle) 36 may be removably secured to the holder 12, such as with threaded connections as shown in FIG. 2, to securely retain the electrode 14 therein during operation. The handle 36 may be provided with various conventional features, such as an aperture through which a sensor cable 38 may be extended, including a conventional strain relief 40 therefor. This combination of handle 36 and strain relief 40 facilitates insertion and removal of the sensor 14 to and from the process fluid flow channel/vessel 18, while helping to prevent damage to either the sensor or its connections to cable 38. In various embodiments this combination is configured to provide a substantially waterproof enclosure for these connections.

With specific reference to FIG. 2, in particular embodiments, one or more seals may be optionally provided to help prevent process fluid from leaking between the various moving parts of assembly 10. For example, external shaft seals 40, e.g., in the form of conventional O-rings, may be disposed between the receptacle 20 and the holder 12 to help prevent process fluid form leaking therebetween. Similarly, internal shaft seals 42, which may also take the form of O-rings, may be disposed between the holder 12 and sensor 14, and between the holder 12 and the optional flange 21. As shown, these internal seals 42 may be axially spaced along the holder 12 on opposite sides of the aperture(s) 16, to help ensure that process fluid passing to the aperture(s) does not leak elsewhere within the holder 12. These seals 40, 42, help to provide a substantially liquid-tight, sliding engagement between the holder 12 and receptacle 20, and between the holder 12 and the sensor 14.

As also shown, in an exemplary embodiment, receptacle 20 includes a stepped central channel having a relatively large transverse dimension disposed at a proximal end portion, and a relatively small transverse dimension disposed at a distal end portion thereof. It is this distal end portion which is configured to form a sliding fit with the electrode holder 12, and within which seals 40 may be disposed. The abutment/ cam surface 32 may be formed in the proximal end portion, and as shown, defines the relatively large transverse dimension to facilitate placement of the axial extension 28 between it and the holder 12.

Another optional feature includes the provision of a wear surface (e.g., ring) 46 extending radially between the relatively large and relatively small transverse dimensions. This wear surface is configured to slidably guide the distal end of the electrode holder 12 towards the center of the channel during insertion thereof into the receptacle 20. Surface 46 may be fabricated from substantially any relatively soft, lubricious material or combination of materials, such as PTFE (polytetrafluoroethylene), PVC (polyvinylchloride), nylon, etc. Substantially any non-metallic material may be used. The wear surface (ring) 46 may thus be used to help center the holder 12 while avoiding metal-to-metal contact, e.g., to prevent galling of the holder against the receptacle 20 during insertion and removal of the sensor 14, as discussed in greater detail below.

It is noted that the foregoing embodiments enable electrochemical sensors of various lengths to be conveniently placed at various depths of insertion within a particular process. These embodiments thus accommodate different length probes and/or allow for adjustment of the depth of insertion between a maximum and minimum. A user may thus easily change the sensor insertion depth, such as to accommodate variable process fluid levels, and/or to take measurements at different levels within the fluid where conditions may vary. These embodiments also enable sensors to be isolated from the process, e.g., for removal and calibration, without the need to shut down the process.

Having shown and described exemplary insertion assemblies of the present invention, a method of operation thereof will now be described. It is noted that for ease of explication, the embodiments of FIGS. 1-5 have been shown with a relatively short sensor 14. It should be reiterated, however, that sensors 14 of various lengths may be used without departing from the scope of the present invention.

As mentioned above, holder 12 is shown in its fully inserted position in FIGS. 1 and 2, in an intermediate fluid insertion position in FIG. 3 in which the sensor may be operated to detect an analyte associated with the process fluid as discussed hereinbelow, and in its fully retracted position in FIG. 4. In FIG. 5, the fully retracted holder 12 is shown with the handle and sensor having been removed therefrom.

Figure 6:
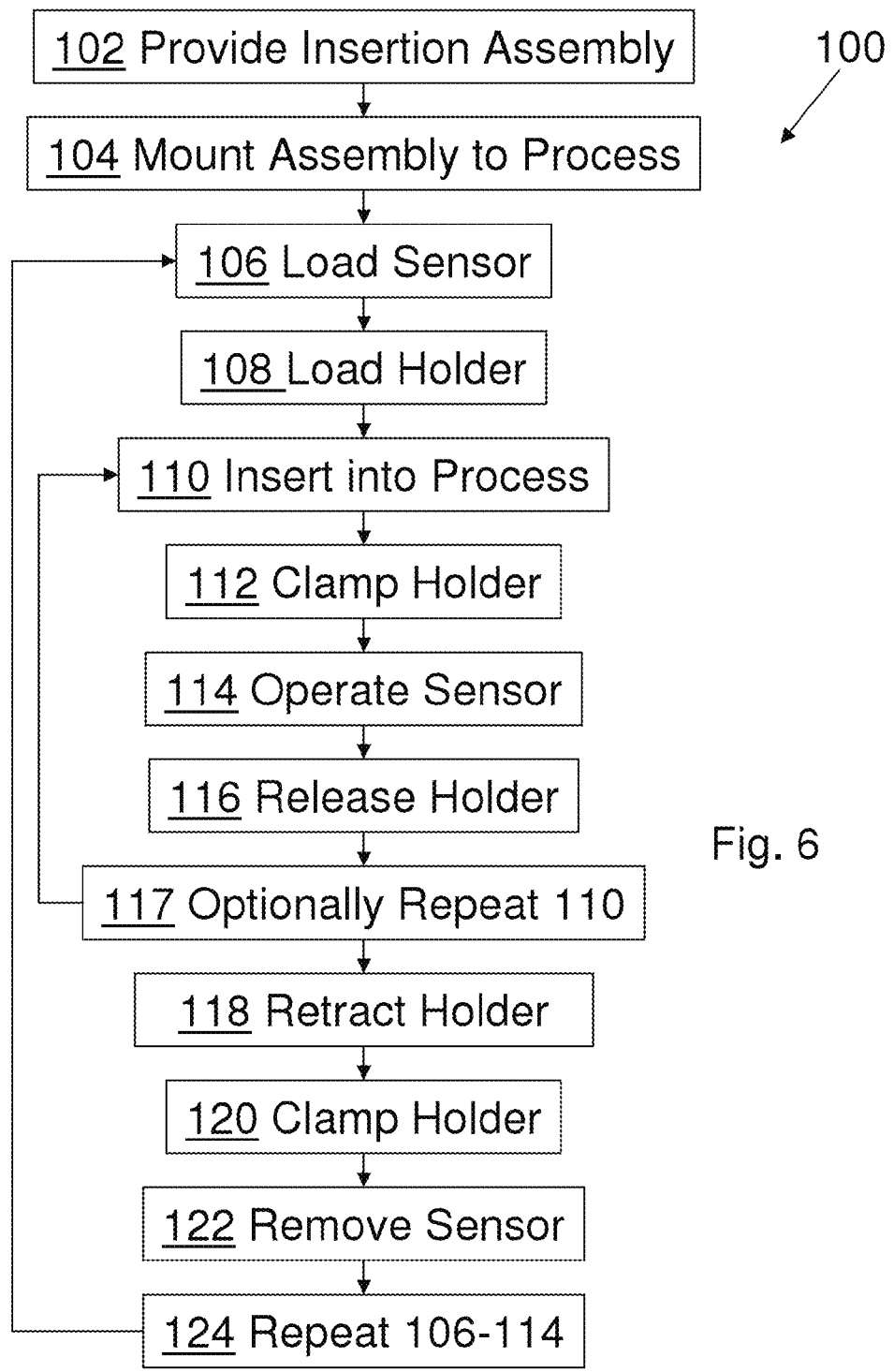
FIG. 6 is a flow chart of an exemplary method in accordance with the present invention.

A method for adjustably inserting a modular electrochemical potential measurement sensor into a process fluid will now be described with reference to the flow chart of FIG. 6. This method 100 includes providing 102 an insertion assembly such as shown and described hereinabove with respect to FIGS. 1 and 2. At 104, the open distal end portion 22 of the receptacle 20 is extended through a wall of a process fluid flow conduit 18. The electrochemical sensor 14 is loaded 106 into the elongated electrode holder 12. The holder 12 may then be slidably loaded 108 into the receptacle 20, so that holder 12 is configured for slidable movement within a range of motion extending from inserted to retracted positions, as shown in FIGS. 2 and 4, respectively. The aperture(s) 16 of the electrode holder 12 is open to process fluid when the electrode holder is disposed in the fully-inserted position (FIG. 2), and closed to the process fluid when in the retracted position (FIG. 4). At 110, the holder 12 is moved into a fluid insertion position disposed at any of a plurality of positions within the range of motion. The tube nut 24 is rotated to clamp 112 the electrode holder 12 in this fluid insertion position. The sensor 14 may then be operated 114 to detect an analyte associated with the process fluid. At 116, the tube nut 24 is counter-rotated to release the electrode holder 12, upon which it may be moved 117 to another insertion position by repeating steps 110-114, or moved 118 into the fully retracted position as shown in FIG. 4. At 120, the tube nut 24 is rotated to clamp the holder 12 in the fully retracted position. The electrochemical sensor may then be removed 122, such as by unscrewing the handle 36 from the holder 12, as shown in FIG. 5. Steps 106-114 may be repeated at 124.

As shown and described in the foregoing embodiments, a tube nut 24 is used to effectively lever the extension 28 and abutment into and out of engagement with one another to effect the desired clamping and unclamping. It should be recognized, however, that substantially any configuration capable of moving cam surface(s) into and out of engagement with one another may be used to clamp and unclamp the sensor, without departing from the scope of the present invention.

It should be understood that any of the features described with respect to one of the embodiments described herein may be similarly applied to any of the other embodiments described herein without departing from the scope of the present invention.

In the preceding specification, the invention has been described with reference to specific exemplary embodiments for the purposes of illustration and description. It is not intended to be exhaustive or to limit the invention to the precise form disclosed. Many modifications and variations are possible in light of this disclosure. It is intended that the scope of the invention be limited not by this detailed description, but rather by the claims appended hereto.

Having thus described the invention, what is claimed is:

1. An adjustable insertion assembly for modular electrochemical potential measurement sensors, the assembly comprising:
    an elongated electrode holder having opposite proximal and distal ends and an opening configured to removably receive therein, through the proximal end of the holder,
    an electrochemical sensor having measurement and reference half cells, the electrochemical sensor configured for electrochemically responding to a process analyte upon contact with a process fluid;
    a receptacle defining an aperture configured to slidably receive the electrode holder therein, wherein the electrode holder is configured for slidable movement within a range of motion extending from a distal inserted position to a proximal retracted position;
    the receptacle having an open distal end portion configured for extension through a wall of a process fluid vessel, wherein the electrode holder is open to the process fluid when the electrode holder is disposed in the inserted position, and closed to the process fluid when in the retracted position;
    a leverage member coupled to the receptacle, and configured for releasable movement relative to the receptacle;
    an extension captured by the leverage member and configured for being moved by the leverage member relative to the receptacle;
    the receptacle having an abutment configured to engage the extension in a sliding, interference fit, so that movement of the leverage member in opposite directions alternately clamps and releases the electrode holder relative to the receptacle to substantially prevent and permit movement at substantially any point within the range of movement;
    a flange disposed at the distal end of the electrode holder, the flange sized and shaped to engage the distal end of the receptacle and prevent further proximal movement of the electrode holder relative to the receptacle when the electrode holder is disposed in its retracted position to provide a mechanical stop for the electrode holder and close the aperture of the receptacle to the process fluid;
    wherein when the electrode holder is in its retracted position, the opening of the holder is closed to the process fluid and the sensor is removable from the opening of the holder through the proximal end of the holder.

2. The assembly of claim 1, wherein the extension and abutment are configured so that mutual engagement moves at least one of the extension and abutment transversely to the axial direction.

3. The assembly of claim 1, wherein the leverage member comprises a tube nut disposed about, and threadably engaged with a proximal end of the receptacle, the tube nut being configured for threaded, axial movement relative to the receptacle, and the extension includes an axial extension configured for moving axially with the tube nut.

4. The assembly of claim 1, wherein the range of motion extends from fully inserted to fully retracted positions, and the electrode holder is open to the process fluid when disposed in any of a plurality of inserted positions within the range of motion.

5. The assembly of claim 1, wherein the electrode holder has an aperture disposed in a distal end portion thereof, to permit process fluid to flow therethrough into contact with the sensor disposed therein.

6. The assembly of claim 1, wherein the electrode holder is sized and shaped to receive therein, electrochemical sensors of a plurality of sizes.

7. The assembly of claim 6, wherein the electrode holder is sized and shaped to receive therein, electrochemical sensors of a plurality of axial dimensions.

8. The assembly of claim 3, wherein the axial extension comprises a wedge having a cam surface extending obliquely to the axial direction.

9. The assembly of claim 8, wherein the abutment comprises another cam surface extending obliquely to the axial direction, and configured for surface to surface engagement with the cam surface of the wedge.

10. The assembly of claim 9, wherein the receptacle comprises a stepped central channel having a relatively large transverse dimension disposed at a proximal end portion, and a relatively small transverse dimension disposed at a distal end portion thereof.

11. The assembly of claim 10, wherein the distal end portion is configured to form a sliding fit with the electrode holder.

12. The assembly of claim 10, wherein the other cam surface is disposed on a wall of the central channel at the proximal end portion thereof.

13. The assembly of claim 12, comprising a wear surface extending radially between the relatively large and relatively small transverse dimensions.

14. The assembly of claim 13, wherein the wear surface is configured to slidably guide the distal end of the electrode holder towards the center of the channel during insertion thereof into the receptacle.

15. The assembly of claim 1, comprising a seal disposed between the flange and the distal end of the receptacle when the electrode holder is disposed in its retracted position, wherein the aperture is out of fluid communication with the process fluid.

16. The assembly of claim 1, further comprising the electrochemical sensor.

17. The assembly of claim 16, wherein the electrochemical sensor is configured for being coupled to a process variable transmitter.

18. The assembly of claim 16 wherein the measuring half-cell comprises a pH electrode.

19. The assembly of claim 16 wherein said measuring half-cell comprises a selective ion electrode.

20. The assembly of claim 16 wherein said measuring half-cell comprises a fluoride ion selective electrode.

21. The assembly of claim 16 wherein said measuring half-cell comprises an oxidation-reduction potential electrode.

* * * * *